United States Patent [19]

Bjostad, III et al.

[11] Patent Number: 5,238,724
[45] Date of Patent: Aug. 24, 1993

[54] ARTHROPODICIDAL USE OF 6-METHOXY-2-BENZOXAZOLINONE COMBINED WITH INSECTICIDES AND/OR BIOCONTROL AGENTS

[75] Inventors: Louis B. Bjostad, III, Bellvue; Bruce E. Hibbard, Fort Collins, both of Colo.

[73] Assignee: Colorado State University Research Foundation, Fort Collins, Colo.

[21] Appl. No.: 866,922

[22] Filed: Apr. 10, 1992

Related U.S. Application Data

[62] Division of Ser. No. 626,888, Dec. 13, 1990, Pat. No. 5,112,843.

[51] Int. Cl.$^5$ .................... A01N 43/76; A01N 63/00; A01N 63/04
[52] U.S. Cl. .................... 424/84; 424/93 Q; 424/93 T; 514/375
[58] Field of Search ............... 514/375; 424/84, 93 Q, 424/93 T

[56] References Cited

U.S. PATENT DOCUMENTS

| | | | |
|---|---|---|---|
| 4,565,695 | 1/1986 | Guss et al. | 424/84 |
| 4,880,624 | 11/1989 | Metcalf et al. | 424/84 |
| 5,112,843 | 5/1992 | Bjostad, III et al. | 514/375 |

OTHER PUBLICATIONS

Hibbard et al., J. Chem. Ecology, 14:1523 to 1539, (1988).
Tseng et al. CAS 113:37834c "Relation to DIMBOA concentration in leaves at various stages of plant growth with resistance of maize to Asian corn borer" (1989).

Primary Examiner—Allen J. Robinson
Assistant Examiner—S. Mark Clardy
Attorney, Agent, or Firm—James A. Costello

[57] ABSTRACT

Control of arthropods, particularly the larvae of Diabrotica spp., by application of 6-methoxy-2-benzoxazolinone (6-MBOA) alone or in combination with an insecticide or biocontrol agent; and arthropodicidal compositions containing 6-MBOA.

27 Claims, No Drawings

ARTHROPODICIDAL USE OF 6-METHOXY-2-BENZOXAZOLINONE COMBINED WITH INSECTICIDES AND/OR BIOCONTROL AGENTS

This is a division of application Ser. No. 07/626,888, filed on Dec. 13, 1990, U.S. Pat. No. 5,112,843.

BACKGROUND OF THE INVENTION

The larvae of three species of Diabrotica beetles are among the most serious insect pests of corn in the United States. These three species include the western corn rootworm, *Diabrotica virgifera virgifera* LeConte, the northern corn rootwor, *Diabrotica barberi* Smith and Lawrence, and the southern corn rootwor, *Diabrotica undecimpunctata howardi* Barber. More insecticide is used for the control of Diabrotica spp. than for any other pest of corn, and the total acreage treated is greater than for any other insect pest in the United States.

Diabrotica larvae emerge in the spring from overwintering eggs laid in the soil the previous fall. After hatching, the neonate larvae move through the soil and locate suitable host roots. There is increasing evidence that host location is facilitated by volatile semiochemicals (chemicals that are used for communication) produced by the corn plant. Cryogenic collections of volatile compounds, including carbon dioxide, that emanate from germinating corn seeds are known to be attractive to rootworm larvae. (Hibbard et al., J. Chem. Ecology, 14:1523 to 1539, 1988).

It has been found that 6-methoxy-2-benzoxazolinone (6-MBOA) is also attractive to corn rootworm larvae and can be used in the management of corn rootworm damage to corn either alone or in combination with other more commonly used insecticides.

SUMMARY OF THE INVENTION

This invention pertains to a method for controlling arthropods, especially corn rootworm, by applying the compound

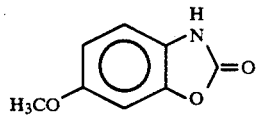

6-methoxy-2-benzoxazolinone (6-MBOA)

to soil that contains the rootworm. For the sake of convenience, the term "corn rootworm(s)" as employed herein should be understood to include all Diabrotica larvae species.

This invention also concerns a method for controlling arthropods, especially corn rootworm, by applying to them or to their environment a composition comprising 6-MBOA and, optionally, an insecticide. Preferred insecticides are those toxic to corn rootworm, including those selected from the group organophosphates, carbamates, pyrethroids, nitromethylene heterocycles (hexahydro-1H-azepine, hexahydro-1H-1,3-diazepine, hexahydro-1,3-oxazepine, hexahydropyrimidine, hexahydro-1,3-thiazepine, imidazolidine, oxazolidine, piperidine, pyridine, pyrrolidine, tetrahydro-2H-1,3-oxazine, tetrahydro-2H-1,3-thiazine, thiazolidine), nitroguanidines and agriculturally suitable mixtures of any one or more members of the group.

Preferred organophosphates are selected from the group chlorethoxyfos, terbufos, chlorpyrifos, chlorpyrifos-methyl, fonofos, chlormephos, EPBP, disulfoton, diazinon, parathion, methyl parathion, phorate, phoxim, pirimiphos-ethyl, temephos, trichloronate, isazophos, ethoprop, phostebupiram and 0,0-diethyl 0-(2(1,1-dimethylethyl)-5-pyrimidinyl) phosphorothioate. Most preferred are chlorethoxyphos, terbufos, chlorpyrifos and fonofos, especially chlorethoxyphos.

Preferred carbamates are selected from the group methomyl, carbofuran, aldicarb, benfuracarb, cloethocarb, furathiocarb, bendiocarb, carbaryl, thiodicarb, and trimethacarb. Most preferred are methomyl and carbofuran.

Preferred pyrethroids are selected from the group allethrin, alphamethrin, bifenthrin, cyfluthrin, cyhalothrin, cypermethrin, deltamethrin, esfenvalerate, fenpropathrin, fenvalerate, flucythrinate, flumethrin, fluvalinate, MTI-500, permethrin, phenothrin, pyrethrins, resmethrin, tefluthrin, tetramethrin and tralomethrin. Most preferred are bifenthrin, cypermethrin, deltamethrin, esfenvalerate, fenvalerate, permethrin, tefluthrin and tralomethrin.

Preferred nitromethylene heterocycles are thiazines such as the tetrahydro-2-(nitromethylene)-2H-1,3-thiazines including their resonance hybrids, geometric isomers, tautomers and mixtures of them.

This invention also concerns a method for controlling arthropods, especially corn rootworm, by applying a composition comprising 6-MBOA and a biocontrol agent such as the protozoan pathogens gregarines and microsporidans, baculovirus, pathogenic fungi or parasitic nematodes belonging to the genus Steinernema to the rootworm-containing soil. Preferred nematodes include *Steinernema feltiae*.

This invention also concerns a composition for controlling arthropods, especially corn rootworm, comprising an admixture of 6-MBOA and an agriculturally suitable carrier. Especially preferred are compositions that contain, in admixture with the 6-MBOA, an insecticide especially one that is toxic to corn rootworm. Preferred classes of insecticides are the organophosphates, carbamates, pyrethroids, nitromethylene thiazines and agriculturally suitable mixtures thereof. Preferred compositions contain 6-MBOA in admixture with one or more of the following: chlorethoxyfos, terbufos, chlorpyrifos, chlorpyrifos-methyl, fonofos, chlormephos, EPBP, disulfoton, diazinon, parathion, methyl parathion, phorate, phoxim, pirimiphos-ethyl, temephos, trichloronate, isazophos, ethoprop and 0,0-diethyl 0-(2(1,1-dimethylethyl)-5-pyrimidinyl) phosphorothioate. Preferred compositions also include those containing 6MBOA in admixture with the organophosphates: chlorethoxyphos, terbufos, chlorpyrifos, fonofos; the carbamates: methomyl, carbofuran, aldicarb, furathiocarb, bendiocarb, carbaryl and thiodicarb; and the pyrethroids: alphamethrin, bifenthrin, cyfluthrin, cyhalothrin, cypermethrin, deltamethrin, esfenvalerate, fenpropathrin, fenvalerate, flucythrinate, flumethrin, fluvalinate, MTI-500, permethrin, phenothrin, pyrethrins, resmethrin, tefluthrin, tetramethrin and tralomethrin.

This invention also concerns a method for surveying for the presence of corn rootworm in a designated area comprising applying 6-methoxy-2-benzoxazolinone in one or more locations in or near the designated area, attracting corn rootworm to said locations, monitoring the presence of corn rootworm at those locations and calculating the extent to which they are present in the designated area.

DETAILS OF THE INVENTION

Examples 1 and 2 demonstrate that 6-MBOA is an important component of the semiochemical blend that attracts corn rootworm larvae to corn. This characteristic as well as the chemical nature of 6-MBOA make it particularly useful as a semiochemical for a soil insect. It has sufficient vapor pressure ($6.5 \times 10^{-4}$ mm Hg, estimated) and water solubility ($K_{o/w} = 10^2$, calculated) to disperse under a variety of soil moisture conditions. In dry soils, 6-MBOA can disperse as a volatile compound in the soil vapor phase. In moist soil, 6-MBOA can disperse in the aqueous phase as a water-soluble compound. This suggested reliability of the chemical signal that 6-MBOA provides can be quite important to corn rootworm larvae, because the larvae must locate a host plant under a wide variety of environmental conditions within 24 hours of hatching in order to survive, and 6-MBOA is well suited as an attractant.

Because of its unique characteristic as a corn rootworm attractant, 6-MBOA is useful in an integrated approach to corn rootworm management. One possible use is as an adjuvant to improve the performance of soil insecticides. It is known that very small percentages of the pesticides applied to crops actually reach the target pests. The development of more efficient means to deliver pesticides to corn pests would have valuable environmental and economic benefits.

Current practices of insecticide application for Diabrotica larvae appear to be very compatible with semiochemical technology for enhancing insecticide performance. Most insecticides in current use for control of corn rootworm larvae are granular formulations. The granules are usually applied at planting time in a band over each row or in the seed furrow from an applicator mounted on the corn planter, and are incorporated into the soil by press wheels or drag chains. Because corn rootworms are likely to encounter an insecticide by chance as they crawl through the soil, it is necessary to establish an effective concentration of the insecticide through a large volume of soil.

Use of 6-MBOA, added to granular insecticide formulations to lure corn rootworm larvae from a distance in the soil, killing them at the site of the granule, will allow improved insect control. With attraction of larvae to the insecticide granule, acceptable levels of control can be achieved with significantly less insecticide. Furthermore, a wider array of insecticides are applicable because there is a reduced need for the insecticide to diffuse an appreciable distance from the site of application since the larvae are attracted to it. Insecticides that are much less toxic to non-target species than those currently used for rootworm control, or those that break down rapidly after they diffuse from the granule, can become practical to use because the major site of control will be at the granule itself. Furthermore, the reduced levels of insecticide in the surrounding soil will encourage beneficial soil organisms, including predaceous nematodes and other biocontrol agents that assist in the control of Diabrotica larvae.

Biocontrol agents such as parasitic nematodes of the genus Steinernema show promise for control of Diabrotica larvae, but survive only a short time in the corn agroecosystem (due to temperature and water stress). Attraction of Diabrotica larvae to a source of the nematodes, facilitated by 6-MBOA, can substantially increase the extent and rate of infection. It can also be possible to manipulate natural soil predator populations, some of which are attracted to the plant on which they prey exist.

Other contemplated biocontrol agents include protozoan pathogens such as gregarines and microsporidans (Jackson, J. J. 1986. "Rearing and handling of *Diabrotica virgifera* and *Diabrotica undecimpunctata howardi*, In Methods for the Study of Pest Diabrotica, Springer-Verlag, New York, Chapter 2.), baculovirus (Kim et al. 1984. J Invertebrate Pathology 43:234–241) and pathogenic fungi (Naranjo et al. 1988. J. Invertebrate Pathology 51:298–300). Because Diabrotica larvae and their predators can be attracted to a common location by using 6-MBOA, naturally-occurring biocontrol can be increased.

Another use of 6-MBOA in the control of Diabrotica larvae is in a confusion strategy. Placing many point sources of an attractant such as 6-MBOA in the soil can act as a behavioral disruptant that disorients the larvae and prevents them from locating corn roots, resulting in death by starvation.

A further use of 6-MBOA to manage Diabrotica larvae is as a survey tool to monitor the population of corn rootworm larvae in a field. Such a tool would give the farmer advance notice of an impending infestation and allow appropriate control measures to be invoked in a timely manner.

EXAMPLE 1

Isolation and Identification of 6-MBOA from Germinating Corn Seeds

To recover the compounds of interest, pregerminated corn seeds (pre-stage 0, 3–5 days old) [Ritchie, et al., Cooperative Extension Service Special Report 48 Iowa State University, Ames, Iowa (1984)] were extracted by placing them in a glass seed-holding tube (30 cm × 30 mm, tapering to 12 mm) for 3–6 hours and then dripping dichloromethane over them until 4 mL of solution had been collected. To determine the attractancy of the extract, tests were conducted in a choice test bioassay arena. The arena consisted of three plastic petri dishes (5 cm diameter) connected in series by Teflon ® tubing (10 mm diameter). Holes (12 mm diameter) were cut into the bottom of the end dishes to allow connection of test tubes. Two pieces of glass wool, one of which was treated with the dichloromethane extract of corn roots, and the other with an equal amount of dichloromethane alone, were placed in the end petri dishes of the bioassay chamber near the mouth of the test tube and distal to the central petri dish. The carbon dioxide concentration in the end petri dishes was adjusted to 4 mmol/mol and the concentration at the beginning of each test was confirmed with a Beckman Model 865 IR gas analyzer. After the dichloromethane had evaporated, ten second-instar western corn rootworm larvae were placed in the center of a small petri dish lid (40 mm diam. With a 5 mm high lip) which was then placed in the center chamber of the bioassay apparatus. The number of larvae in each of the three petri dishes was recorded at 60 minutes. Under these test conditions, significantly more larvae were attracted to the side of the bioassay chamber containing the dichloromethane extract of corn than to the side containing the dichloromethane alone. Pentane extracts of germinating corn were tested in the same way, but no significant difference in choice was observed. This indicated that the compound(s) of interest were relatively polar since they could be extracted with dichloromethane, but not pentane.

The dichloromethane extract of corn roots was separated into fractions by column chromatography on silica gel and eluted batchwise with mixtures of dichloromethane:diethyl ether (100:0, 97:3, 90:10, 75:25, 50:50, and 0:100). The most active fraction as determined in choice-test bioassays with equal concentrations of carbon dioxide was the 75:25 fraction. Analysis of the 75:25 fraction by gas-liquid chromatography (GLC, 3% OV-101 packed column, 2 mm×2 mm, temperature programmed from 60° to 260° at 10°/min, 1 min delay) indicated a major peak at 16.4 min. The peak had a broad tailing edge, consistent with a polar, volatile compound. A large amount of this compound was purified by GLC collections from the same OV-101 column.

The purified compound was analyzed by [$^1$H]NMR with a Bruker AM 500 (500 Mhz) and the spectrum included 5-H 6.70 ppm (dd), 7-H 6.82 ppm (d), 4-H 6.93 ppm (d), 3.79 ppm (s). $J_{5,4}=8.6$ Hz, $J_{7,5}=2.3$ Hz, $J_{4,5}=8,6$ Hz, $J_{5,4}=2.3$ Hz. This suggested a trisubstituted aromatic ring, with a methoxy group as one of the substituents. Both electron-impact (EI, 70 eV) and chemical ionization (CI, $NH_4^+$) mass spectra were obtained with a VG Model MM-16F mass spectrometer (MS) (VG, Inc., Danvers, Mass.). The EI mass spectrum included peaks [m/z (Relative Intensity)] at 165 (100), 150 (63), 136 (4), 122 (11), 109 (16), 106 (34), and 80 (15). The base peak at m/z 165 indicated the presence of a nitrogen atom because of the odd mass, and suggested an empirical formula of $C_8H_7O_3N$. The CI mass spectrum included peaks at 183 (100, M+$NH_4$), 166 (33, M+1), 165 (50), 153 (2), 139 (2), 124 (5), 106 (4). These data were consistent with the structure of 6-MBOA. A synthetic sample of 6-MBOA was analyzed by NMR, EI-MS, and CI-MS as described above, and the spectra were in full agreement with those of the purified, unknown compound from the corn root volatile mixture. A sample of synthetic 6-MBOA was analyzed by GLC, and the retention time matched that of the purified attractive compound from the corn extract.

EXAMPLE 2

Demonstration of the Attractancy of Synthetic 6-MBOA for Western Corn Rootworm Larvae A test arena similar to the choice-test bioassay apparatus previously described was used to determine the attractancy of synthetic 6-MBOA for western corn rootworm larvae. Serial dilutions of 6-MBOA in dichloromethane were pipetted onto pieces of glass wool. After the solvent had evaporated, the treated piece of glass wool was placed in one side of the bioassay chamber near the mouth of the test tube and distal to the central petri dish. The petri dish on the other side of the bioassay chamber contained a piece of glass wool which had been treated with dichloromethane alone. The carbon dioxide concentration in the end petri dishes was adjusted to 4 mmol/mol and the concentration at the beginning of each test was confirmed with a Beckman model 865 IR gas analyzer. Ten second-instar western corn rootworm larvae were placed in the center of a small petri dish lid (40 mm diam. with a 5 mm high lip) which was then placed in the center chamber of the bioassay apparatus. The number of larvae in each of the three petri dishes was recorded at 60 minutes. Percent response was determined by the following relationship:

$$\text{Percent response} = \frac{n_1 - n_2}{10} \times 100$$

where
$n_1$=number of larvae in the 6-MBOA chamber
$n_2$=number of larvae in the control chamber.

For each dose of 6-MBOA, 10 larvae were used for each test, and each test was replicated at least 8 times. Data were analyzed by the statistical program MSTAT (Department of Crop and Soil Sciences, Michigan State University, East Lansing, Mich. 48824). Differences between the number of larvae in the two sides of the bioassay chamber were used in analysis of variance (ANOVA) for these paired data. All data were analyzed with one-way ANOVA. Ninety-five percent confidence intervals were then calculated using the error mean square from the ANOVA table [Snedecor et al., *Statistical Methods* 7th edition Iowa State University Press, Iowa State University, Ames, Iowa, page 507 (1980)] for data sets with more than two means. The bioassays were performed in dim light. To prevent possible effects from previous testing, larvae were not reused in the bioassays. More larvae chose the side containing 6-MBOA between doses of 7.0–700.0 ng, but not at 7 ng or 7.-0 μg. The percent response was significantly different from zero at 7.0 and 700 ng, but not at the other doses tested.

We claim:

1. A method for controlling arthropods, by applying to them or to soil containing them an effective amount of 6-methoxy-2-benzoxazolinone together with an insecticide selected from one or more members of the group carbamates, pyrethroids, nitromethylene heterocycles and nitroguanidines.

2. A method according to claim 1 wherein the arthropods comprise corn rootworm.

3. A method according to claim 2 for controlling corn rootworm selected from the group Southern, Western and Northern corn rootworm.

4. A method according to claim 2 wherein the insecticide is a carbamate.

5. A method according to claim 4 wherein the carbamate is selected from methomyl, carbofuran, aldicarb, furathiocarb, bendiocarb, carbaryl and thiodicarb.

6. A method according to claim 5 wherein the carbamate is selected from methomyl and carbofuran.

7. A method according to claim 2 wherein the insecticide is a pyrethroid.

8. A method according to claim 7 wherein the pyrethroid is selected from allethrin, alphamethrin, bifenthrin, cyfluthrin, cyhalothrin, cypermethrin, deltamethrin, esfenvalerate, fenpropathrin, fenvalerate, flucythrinate, flumethrin, fluvalinate, MTI-500, permethrin, phenothrin, pyrethrin, resmethrin, tefluthrin, tetramethrin and tralomethrin.

9. A method according to claim 8 wherein the pyrethroid is selected from bifenthrin, cypermethrin, deltamethrin, esfenvalerate, fenvalerate, permethrin, tefluthrin and tralomethrin.

10. A method according to claim 2 wherein the insecticide is a nitromethylene heterocycle.

11. A method according to claim 10 wherein the heterocycle is a thiazine.

12. A method according to claim 11 wherein the insecticide is tetrahydro-2-(nitromethylene)-2H-1,3-thiazine.

13. A method according to claim 1 that comprises applying, in addition, an effective amount of a biocontrol agent selected from the group protozoan pathogens, baculovirus, pathogenic fungi and parasitic nematodes.

14. A method according to claim 13 wherein the biocontrol agent is a parasitic nematode belonging to the genus Steinernema.

15. A method according to claim 14 wherein the nematode is *Steinernema feltiae*.

16. A method according to claim 13 that comprises controlling corn rootworm.

17. A composition for controlling arthropods comprising an effective amount of an admixture of 6-methoxy-2-benzoxazolinone together with an insecticide selected from one or more numbers of the group carbamates, pyrethroids, nitromethylene heterocycles, and nitroguanidines in an agriculturally suitable carrier therefor.

18. A composition according to claim 17 wherein the insecticide is a carbamate.

19. A composition according to claim 18 wherein the carbamate is selected from methomyl, carbofuran, aldicarb, furathiocarb, bendiocarb, carbaryl and thiodicarb.

20. A composition according to claim 19 wherein the carbamate is selected from methomyl and carbofuran.

21. A composition according to claim 17 wherein the insecticide is a pyrethroid.

22. A composition according to claim 21 wherein the pyrethroid is selected from allethrin, alphamethrin, bifenthrin, cyfluthrin, cyhalothrin, cypermethrin, deltamethrin, esfenvalerate, fenpropathrin, fenvalerate, flucythrinate, flumethrin, fluvalinate, MTI-500, permethrin, phenothrin, pyrethrin, resmethrin, tefluthrin, tetramethrin and tralomethrin.

23. A composition according to claim 22 wherein the pyrethroid is selected from bifenthrin, cypermethrin, deltamethrin, esfenvalerate, fenvalerate, permethrin, tefluthrin and tralomethrin.

24. A composition according to claim 17 wherein the insecticide is a nitromethylene heterocycle.

25. A composition according to claim 24 wherein the insecticide is a nitromethylene thiazine.

26. A composition according to claim 25 wherein the insecticide is tetrahydro-2-(nitromethylene)-2H-1,3-thiazine.

27. A composition according to claim 17 comprising, additionally, an effective amount of a biocontrol agent selected from the group protozoan pathogens, baculovirus, pathogenic fungi and parasitic nematodes.

* * * * *